(12) United States Patent
Yantasee et al.

(10) Patent No.: US 8,679,458 B2
(45) Date of Patent: Mar. 25, 2014

(54) FUNCTIONALIZED MAGNETIC NANOPARTICLE ANALYTE SENSOR

(75) Inventors: Wassana Yantasee, Richland, WA (US); Maryin G. Warner, Richland, WA (US); Cynthia L. Warner, Richland, WA (US); Raymond S. Addleman, Benton City, WA (US); Glen E. Fryxell, Kennewick, WA (US); Charles Timchalk, Kennewick, WA (US); Mychailo B. Toloczko, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 1615 days.

(21) Appl. No.: 11/936,405

(22) Filed: Nov. 7, 2007

(65) Prior Publication Data

US 2011/0263924 A1   Oct. 27, 2011

(51) Int. Cl.
*G01N 27/12*   (2006.01)
*G01N 27/26*   (2006.01)

(52) U.S. Cl.
USPC ........... 424/9.2; 422/68.1; 436/526; 205/792; 424/9.32; 424/9.323; 424/9.36; 424/9.42

(58) Field of Classification Search
None
See application file for complete search history.

(56) References Cited

U.S. PATENT DOCUMENTS

| | | | | |
|---|---|---|---|---|
| 4,523,996 | A * | 6/1985 | Charles et al. | 210/504 |
| 5,102,527 | A * | 4/1992 | Shibata et al. | 204/416 |
| 7,186,398 | B2 | 3/2007 | Andres et al. | |
| 2002/0177143 | A1 | 11/2002 | Mirkin et al. | |
| 2003/0129608 | A1 * | 7/2003 | Mirkin et al. | 435/6 |
| 2004/0086885 | A1 | 5/2004 | Lee et al. | |
| 2005/0100930 | A1 * | 5/2005 | Wang et al. | 435/6 |
| 2005/0142063 | A1 * | 6/2005 | Batich | 424/9.1 |

OTHER PUBLICATIONS

YT Wu, YC Chen. "Determination of calcium in complex samples using functional magnetic beads combined with electrodeless/sheathless electrospray ionization mass spectrometry." Rapid Communications in Mass Spectrometry, vol. 20, 2006, pp. 1995-1999 and one additional page showing publication date.*

Yavuz, Cafer T.; Low-Field Magnetic Separation of Monodisperse Fe304 Nanocrystals; Science Magazine, www.sciencemag.org; Nov. 10, 2006; vol. 314; pp. 964-967.

Yantasee, Wassana; Warner, Cynthia L.; Sangvanich, Thanapon; Addleman, R. Shane; Carter, Timothy G.; Wiacek, Robert J.; Fryxell, Glen E.; Timchalk, Charles; Warner, Marvin G.; "Removal of Heavy Metals from Aqueous Systems with Thiol Functionalized Superparamagnetic Nanoparticles", Environmental Science & Technology, Aug. 9, 2007; vol. 41, No. 14, pp. 5114-5119.

* cited by examiner

*Primary Examiner* — Frederick Krass
*Assistant Examiner* — Isaac Shomer
(74) *Attorney, Agent, or Firm* — A. J. Gokcek; Derek H. Maughan

(57) ABSTRACT

A method and system for simply and efficiently determining quantities of a preselected material in a particular solution by the placement of at least one superparamagnetic nanoparticle having a specified functionalized organic material connected thereto into a particular sample solution, wherein preselected analytes attach to the functionalized organic groups, these superparamagnetic nanoparticles are then collected at a collection site and analyzed for the presence of a particular analyte.

13 Claims, 2 Drawing Sheets

FUNCTIONALIZED MAGNETIC NANOPARTICLE ANALYTE SENSOR

STATEMENT AS TO RIGHTS TO INVENTIONS MADE UNDER FEDERALLY-SPONSORED RESEARCH AND DEVELOPMENT

This invention was made with Government support under Contract DE-AC0576RLO1830 awarded by the U.S. Department of Energy, as well as a Project BioShield grant from NIAID, grant 1R21 OH008900-01 from NIOSH. The Government has certain rights in the invention.

BACKGROUND OF THE INVENTION

1. Field of the Invention

The invention generally relates to analytical systems and more particularly to systems for detecting and quantifying small amounts of a particular analyte in a relatively large sample volume.

2. Background Information

In the field of analyte detection, a variety of types of methods and devices have been utilized in attempts to obtain correct, reliable and sensitive results related to the quantity and quality of various materials in particular environments. In particular, in applications such as environmental monitoring or healthcare, a need has arisen for a sensitive system that can easily, efficiently and cost effectively determine the quantity of particular materials in a preselected sample, with desired levels of sensitivity, accuracy, precision and reliability. Of particular concern are systems for identifying and quantifying heavy metals, such as mercury, lead, thallium, cadmium, and arsenic because of their adverse impacts to environmental and human health. Prior art sensor systems for such materials typically suffer from any of a number of various deficiencies, including slow mass transport of metal ions to an electrode surface, and reduced effectiveness of the device in environments such as complex biological matrices or natural waters where particular analytes may be bound to organic molecules or proteins.

Therefore a method and/or device is needed that allows for direct, simple, and efficient monitoring of desired analytes in various environments such as biological samples and natural waters. What is also needed is a system and device that allows for simple effective and efficient collection and preconcentration of desired analytes in a variety of environments. The present invention provides these and other advantages.

Additional advantages and novel features of the present invention will be set forth as follows and will be readily apparent from the descriptions and demonstrations set forth herein. Accordingly, the following descriptions of the present invention should be seen as illustrative and not as limiting in any way.

SUMMARY

The present invention is a method and system for simply and efficiently determining quantities of a preselected material in a particular solution. Generally, the method of the present invention is characterized by the placement of at least one superparamagnetic nanoparticle having a specified functionalized organic material connected thereto into a particular sample solution. These functionalized organic molecules are adapted to adhere to a preselected material which may be present in the solution. After placement of these superparamagetic nanoparticles into the solution, the designated materials that are located within the solution attach to the functional organic molecules on the surface of the superparamagnetic nanoparticles. These superparamagnetic nanoparticles are then collected utilizing a collection device and analyzed to determine the quantity of preselected materials within the solution.

A variety of modifications and alterations of this basic idea are contemplated as a part of the present invention. The superparamagnetic particles of the present invention may be placed and arranged in a variety of ways within the solution. This includes not only the dispersion method which is described more fully in the detailed description that follows, but also includes the attachment of these superparamagnetic nanoparticles to a variety of types of fixed and semi fixed locations as well. In addition, various methods for analyzing features of a particular analyte may also be employed and are not excluded or limited by the description of the particular methods and devices that are mentioned herein. The purpose of the foregoing abstract is to enable the United States Patent and Trademark Office and the public generally, especially the scientists, engineers, and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

Various advantages and novel features of the present invention are described herein and will become further readily apparent to those skilled in this art from the following detailed description. In the preceding and following descriptions I have shown and described only the preferred embodiment of the invention, by way of illustration of the best mode contemplated for carrying out the invention. As will be realized, the invention is capable of modification in various respects without departing from the invention. Accordingly, the drawings and description of the preferred embodiment set forth hereafter are to be regarded as illustrative in nature, and not as restrictive.

DETAILED DESCRIPTION OF THE INVENTION

The following description includes the preferred best mode of one embodiment of the present invention. It will be clear from this description that the invention is not limited to these illustrated embodiments but that the invention also includes a variety of modifications and embodiments thereto. Therefore the present description should be seen as illustrative and not limiting. While the invention is susceptible of various modifications and alternative constructions, it should be understood, that there is no intention to limit the invention to the specific form disclosed, but, on the contrary, the invention is to cover all modifications, alternative constructions, and equivalents falling within the spirit and scope of the invention as defined in the claims.

Figure 1:
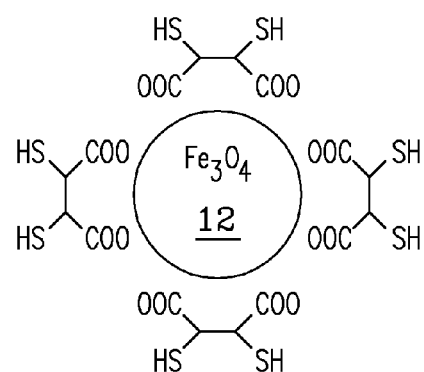
FIG. 1 is a representational view of the superparamagnetic nanoparticle of the preferred embodiment of the present invention.

FIGS. 1-4 show a variety of views and features of a preferred embodiment of the present invention. Referring first to FIG. 1, a superparamagnetic iron oxide ($Fe_3O_4$) nanoparticle 10 with a functionalized surface of dimercaptosuccinic acid (DMSA) 12 is shown. While this preferred embodiment of the present invention includes an iron oxide nanoparticle with a functionalized surface of DMSA it is to be distinctly understood that the invention is not limited to this particular embodiment and that other nanoparticle materials such as metal or metal coated particles made from a variety of materials such as nickel, tantalum, molybdenum, iron oxide, or other types of magnetic, diamagnetic, ferromagnetic, paramagnetic, antiferromagnetic, ferromagnetic materials and superparamagnetic coatings, and combinations thereof may be utilized according to the particular needs and necessities of the user. In addition, various other types of functionalized groups 12 and materials may also be connected to the surface of the superparamagnetic nanoparticles 10 according to the needs and necessities of a user. For example, in some other embodiments the superparamagnetic nanoparticles may be optionally functionalized with a variety of organic groups such as thiol linked to polyethylene glycol (PEG), acteamide phosphoric acid, ethylenediaminetetraacetic acid, hydroxyl pyridinone, glutathione or other materials equipped with a PEG linkage between the particle and a functional organic molecule that adheres to a preselected material.

These superparamagnetic nanoparticles 10 of the preferred embodiment of the present invention are highly dispersible and stable in solution, have large surface area (114 $m^2$/g), and a high functional group content (1.8 mmol thiols). In one embodiment of the invention these materials are dispersed into preselected solution, where various preselected analytes are grabbed by the functionalized surface of the nanoparticles. These nanoparticles are subsequently collected by a magnetic collection device and analytical detection of the analytes can then be performed. While the preferred embodiment of the invention describes the use of these materials as being dispersed throughout a solution, it is to be distinctly understood that this is merely a recitation of one embodiment of one variation of the present invention and that a variety of other configurations may also be included and described according to the needs and necessities of the user.

Figure 2:
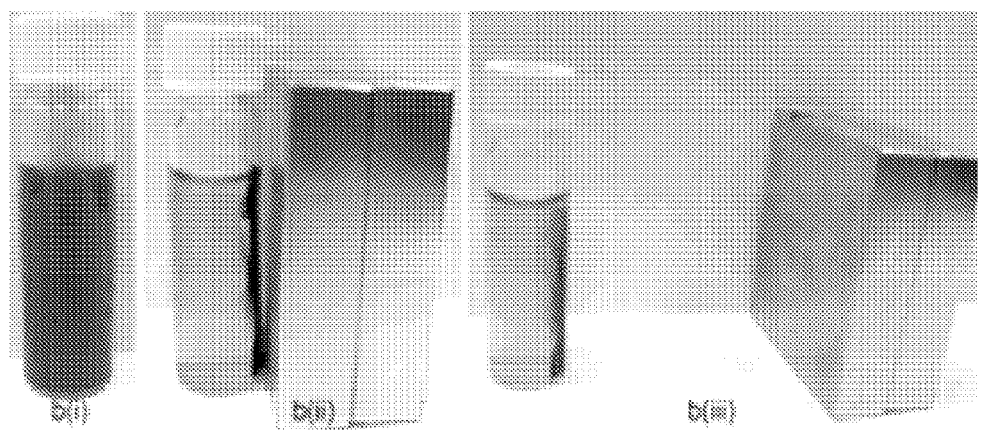
FIG. 2 is a photograph demonstrating dispersion and collection of the superparamagnetic nanoparticles of the preferred embodiment of the present invention.

FIG. 2 shows one application of the use of the superparamagnetic nanoparticles 10 described above. In one preferred embodiment of the invention, these superparamagnetic nanoparticles 10 are dispersed into a particular solution and mixed therein. After dispersion into the solution, these nanoparticles 10 are capable of attraction to a magnetic field and can be separated from this solution in a short period of time (typically less than one minute) with a magnetic device for further analysis. As will be discussed in further detail below, these materials and various methods for their use demonstrate a chemical affinity, capacity, kinetics and stability that is significantly greater than or equal to other diagnostic methodologies and devices including conventional resin based sorbents (GT-73), activated carbon, and nanoporous silica (SAMMS™) of similar surface chemistries in solutions such as river water, groundwater, seawater, and human blood and plasma.

The creation of the superparamagnetic nanoparticles 10 described in the preferred embodiment was accomplished by preparing a bare iron oxide nanoparticle using a modified co-precipitation method. While this particular method of preparing this material is described it is to be distinctly understood that the invention is not limited thereto but may be variously prepared and configured according to the particular needs and necessities of the user. Therefore the following example should be viewed as merely illustrative and not as limiting in any way. In one embodiment, Fe (III) and Fe (II) salts (in a 2:1 mole ratio) were dissolved in deionized water to form an iron salt solution. Addition of 1.5 M NaOH to the iron salt solution caused the immediate formation of iron oxide nanoparticles. After stirring for 10 minutes, the nanoparticles were washed repeatedly with water, dried under vacuum and stored under argon until use. In this preferred embodiment, the particles have an average diameter of ~6 nm-7 nm; however, it is to be distinctly understood that various other sizes ranging up to 1 mm may also be employed according to the particular needs and necessities of the user.

After formation, the iron oxide nanoparticles 10 of this preferred embodiment were then connected to the DMSA surface material by high temperature reaction of tris(acetylacetonato)iron(III) ($Fe(III)(acac)_3$) in the presence of a stabilizing surfactant. $Fe(III)(acac)_3$ (2 mmol), 1,2-hexadecanediol (10 mmol), lauric acid (6 mmol), and laurylamine (6 mmol) were dissolved in 20 mL of benzyl ether and heated to 300° C. at a rate of 4° C./minute. The solution was refluxed for 30 minutes, cooled to room temperature, and 30 mL of ethanol was added. A black solid was collected by centrifugation from these materials. The resultant organic soluble crystalline nanoparticles ($d_{avg}$=5.8 nm±0.9 nm as determined by size analysis of TEM images) were washed several times with ethanol and magnetically purified to remove any remaining starting material and impurities.

A ligand exchange reaction was then used to introduce the meso-2,3-dimercaptosuccinic acid (DMSA) ligand that renders the nanoparticle water-soluble. The surfactant-stabilized nanoparticles were suspended in toluene at 10 (w/v) % and added to a solution of DMSA that was dissolved in DMSO, also at 10 (w/v) % at a 1:1 volume ratio of each solution. The mixture was placed on a vortex and shaken vigorously for 24 hours. The toluene layer was then discarded yielding water-soluble DMSA-functionalized iron oxide nanoparticles (DMSA-$Fe_3O_4$) dissolved in DMSO. The nanoparticles were purified using multiple water washes with magnetic separation of particles from the supernatant. The final water-soluble product was stored at 4° C. as a dry black powder prior to use in the metal extraction experiments. The surface properties of the preferred embodiment of the invention created above are as follows:

| Properties | Analytical method | Values |
| --- | --- | --- |
| Particle size | TEM | 5.8 ± 0.9 nm |
| Surface area | BET | 114 $m^2$/g |
| $Fe_3O_4$ content | ICP-MS of Fe | 3.5 ± 0.1 mmol/g |
| DMSA content | ICP of S | 0.9 ± 0.1 mmol/g |

Figure 3:
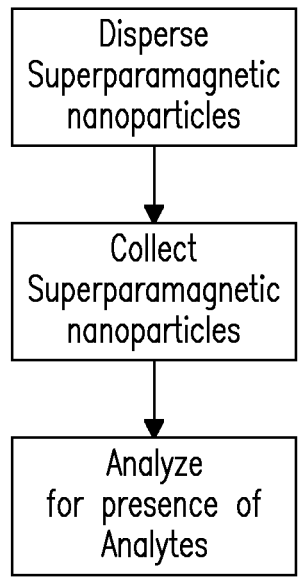
FIG. 3 is a flow chart demonstrating one method of the preferred embodiment of the present invention.
Figure 4:
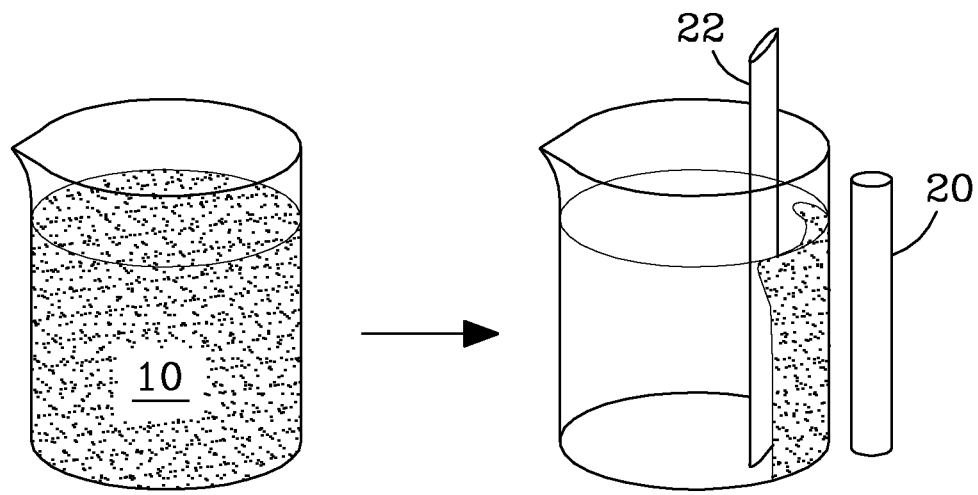
FIG. 4 is schematic device for performing the method described in the preferred embodiment of the present invention.

FIG. 3 shows a flow chart of a method for utilizing the functionalized superparamagnetic nanoparticles 10 of the present invention. This method includes the steps of dispersing the superparamagnetic nanoparticles 10 into a solution for a period of time (normally within minutes) so that they can capture the analytes, collecting these superparamagnetic nanoparticles that is bound with the analytes 10 utilizing a collection device, and analyzing analytes bound to the collected superparamagnetic nanoparticles 10 to determine the quantity of a particular analyte. A system for performing these steps is shown in FIG. 4. Such a system would comprise the functionalized superparamagnetic nanoparticles 10, a device for collecting these particles 20 and a device for analyzing a particular analyte bound to these collected particles 22. These pieces may be configured in a variety of ways including portable monitors that may be easily transported from one location to another for simple monitoring. In addition to these designated pieces, a variety of other types of features and devices may also be connected to this system.

In equilibrium experiments to evaluate the affinity of the functionalized superparamagnetic nanoparticles to various metals, liquid samples consisting each of seawater, river water, ground water and human plasma were spiked with metal ions to obtain 0.5 ppm (each) of multi-component Co, Cu, As, Ag, Cd, Hg, Tl, and Pb, and were aliquoted into 10 mL volumes in a 15 mL polypropylene tube. Each sample was then spiked with a small volume of nanoparticles suspended in DI water to obtain a desired liquid per solid ratio (L/S with units of mL/g throughout) without significantly altering the sample matrix. The sample was then agitated for 2 hrs at 160 rpm on an orbital shaker. After 2 hrs, each tube was then placed on the face of a 1.2 T Neodymium Iron Boron (NdFeB) magnet. All of the nanoparticles in the tube migrated toward the magnet in ~10 seconds. After 30-60 seconds, the supernatant was removed and kept in 1 vol. % $HNO_3$ prior to metal analysis. At this particle size (6 nm-7 nm), it can be observed that the magnetic removal of the nanoparticles from the liquid phase was nearly as effective as, yet faster than centrifugation.

The collection of the superparamagnetic nanoparticles 10 at a magnetic-based electrode surface prior to detection allows analytes such as metal ions to be preconcentrated rapidly at an open circuit without sample pretreatment or the adding of electrolytes. The present invention also allows for the detection of metals in biological samples using electrochemical sensors with high accuracy and sensitivity without various sample pretreatments required by prior art methods. For example, the present invention eliminates the necessity of acid elution or solvent extraction to release metals from proteins followed by metal preconcentration at a mercury-film electrode, the use of internal standards at Hg-based electrodes, or the use of sonication at the polymeric film-coated mercury-film electrode coupled with large sample dilution to minimize protein adsorption and promote mass transport of metals to the sensor surface. While the present invention allows for these steps and for the use of toxic Hg based electrodes to be excluded, it is to be distinctly understood that several of these steps may also be included depending upon the particular needs and necessities of the user.

The chemical binding affinity of a sorbent can be expressed in terms of the distribution coefficient ($K_d$). The higher the $K_d$ value, the more effective the sorbent material is at capturing and holding the target species. In general, $K_d$ values of ~$10^3$ mL/g are considered good and those above $10^4$ mL/g are outstanding. In a comparison study, the DMSA-$Fe_3O_4$ nanoparticles of the preferred embodiment of the present invention, and three commercial sorbents, including Duolite® GT-73 resins, Chelex-100 resin, Darco® KB-B activated carbon, and a self-assembled thiol monolayer on mesoporous support (SH-SAMMS™) were tested for comparison in various aspects.

The results of this testing showed that in terms of affinity the DMSA-$Fe_3O_4$ of the present invention is significantly superior to the commercial GT-73 and activated carbon (Darco KB-B) for capturing Hg, Cd, Ag, Pb, and Tl. The distribution coefficient of DMSA-$Fe_3O_4$ for As was more modest than for other metals and similar to that on unmodified $Fe_3O_4$. When compared to the commercial sorbents tested, both DMSA-$Fe_3O_4$ and SH-SAMMS™ are outstanding sorbents for Pb, Hg, Cd, Cu, and Ag. The large surface area of the DMSA-$Fe_3O_4$ (114 $m^2/g$) and SH-SAMMS™ (74 $m^2/g$) afforded a high number of ligands on the materials, leading to a large ion loading capacity. The maximum Hg sorption capacity of DMSA-$Fe_3O_4$ was 227 mg Hg/g (0.010 mmol Hg/$m^2$), which was comparable with that of SH-SAMMS™ (measured to be 167 mg Hg/g or 0.011 mmol Hg/$m^2$ in this matrix), but 30-fold larger than that of GT-73 (8 mg Hg/g or 0.001 mmol Hg/$m^2$).

The absence of internal diffusion resistance in the nanoparticles in this preferred embodiment of the present invention leads to the sorption kinetics that were observed to be as rapid as those on SH-SAMMS™. In addition to stability and efficacy in a variety of types of matrices, the present invention further demonstrates implication in clinical applications because of the absence of iron leaching in human plasma. While these nanoparticles of the preferred embodiment of the present invention are stable in these environments, the digestion of metal-bound magnetic nanoparticles in order to recover the metals would be relatively easy. For example, digestion in 5 M acid at room temperature would accomplish such a result.

In addition to the analytical performance features of the present invention, the superparamagnetic characteristic of the present invention provides for a variety of other advantages as well. First, this allows these particles to be magnetically manipulated. This provides a variety of advantages in easy capture and recovery of the materials in various embodiments and allows for selective preconcentration and collection of these materials in a variety of embodiments. Second, in some embodiments, the present invention may also be utilized as a new alternative chelating agent for Pb that offers an advantage over the currently existing FDA-approved liquid DMSA products because particular embodiments of the present invention may be utilized in a method whereby particles within the blood may be cleared directly from blood and plasma by bypassing the kidney with an applied magnetic field.

In one configuration, the superparamagnetic particles of the present invention 10 were tested in a method for sensing toxic metals such as lead (Pb) in a urine matrix. While this particular test and result are described, it is to be distinctly understood that the invention is not limited to similar use but may be variously embodied according to the particular needs and necessities of a user.

Collection of the nanoparticles may be obtained in any of a variety of ways. In experiments conducted by the inventors, two classes of working electrodes, a permanent magnetic electrode and an electromagnetic electrode were utilized. While these demonstrative examples have been provided, it is to be distinctly understood that the invention is not limited thereto but may be variously embodied according to the needs and necessities of the user. In the experiments performed by the inventors, the permanent magnetic electrode consisted of a neodymium cylinder magnet that was press-fit into a PTFE cylindrical tube. The magnet was connected to a copper wire for electrical connection on one end. On the other end, it was packed with carbon graphite paste to about 1 mm depth from the liquid interface. The surface of carbon paste was smoothed on a weighing paper and a very thin-layer was replaced after each measurement. The permanent magnetic electrode yielded the magnetic field strengths of 1700, 1000, 370, and 180 gauss, measured at 0, 1, 3, and 5 mm from the electrode-liquid interface.

The electromagnetic electrode utilized in one set of experiments consisted of a 3 mm dia×80 mm L ferromagnetic rod (80Ni-15.5Fe-4.5Mo) with approximately 800-850 windings of oxygen-free high conductivity (OFHC) insulated copper wire (0.3 mm dia) wrapped over 25 mm length of the rod near the electrode tip. The tip was made of glassy carbon (3 mm dia.×1.5 mm depth) to minimize the physisorption of the nanoparticles which was found to be severe at carbon paste electrode surface. When applying a current of 1.3 ampere (coil resistance of 2.3 ohms), the electromagnetic electrode yielded magnetic field strengths of 494, 320, 175, and 115 gauss, measured at 0, 1, 3, and 5 mm from the electrode-liquid interface. Both of these types of magnetic collection devices functioned appropriately to collect the nanoparticles of the present invention from the solution in which they were placed. Aggregation induced by the magnetic filed is reversible once the field is removed. Thus, the nanoparticles have the advantages of high surface area and magnetic collectability under a reasonable field gradient.

Due to the strong magnetic field, a permanent magnet sensor may not allow the release of $DMSA-Fe_3O_4$ from the electrode surface once a measurement was completed. Thus, the permanent surface magnet sensor must be manually renewed by replacing a material present on the electrode. In this preferred embodiment the material was a thin layer of the carbon paste. While this material is described in one embodiment, it is to be distinctly understood that the invention is not limited thereto but may be variously configured according to the needs and necessities of the user. The electromagnetic electrode described previously however can alternatively hold or release the superparamagnetic nanoparticles. By turning the current to the copper coils on and off to alternatively capture or release the nanoparticles at the electrode surface, automation of the present method is possible.

In addition to these described collection devices, a variety of other types of collection devices may also be utilized. These include, but are not limited to, magnetic flux conductors, nickel foam columns, tantalum foam, molybdenum foam, aluminum foam, metal coated carbon foam or other types of metal foam, flow through traps, and magnetic flow through chambers. In addition various other steps may also be employed to achieve increased capture of materials. These additional steps may include, but are not limited to, steps such as perfusing a sample containing the preselected materials, rapidly recirculating a sample over the capture device, alternating forward and reverse flow directions of a sample, alternately releasing and recapturing the particles, amending a sample with certain chemicals to improve capture including acid/base for pH adjustment, surfactants to minimize particle agglomeration/loss. Obtaining the release of a material from these collection locations may also be obtained by various chemical, mechanical, or electromagnetic means. These include, but are not limited to, increasing solution temperature, changing solution pH, changing solution ionic strength, changing solution ethanol-to-water ratio, changing solution composition to include chemicals such as DNAse, RNAse illuminating particles with ultraviolet light to cleave a linker arm, releasing the preselected material from particles, recapturing the particles for reuse via magnetic capture, filtration, gravity or other methods.

Various methodologies may be utilized to detect the particular analytes that may be collected by the superparamagnetic nanoparticles of the present invention. While some methodologies and instruments are described in the following paragraphs in conjunction with one embodiment of the present invention, various other types of methodologies and materials are contemplated as a part of the invention and may be included depending upon the needs and necessities of a user. Examples of additional types of methods and devices that could be used in the present invention include, but are not limited to, absorption, reflectance, fluorescence in a variety of spectra including ultraviolet, infrared, near infrared, and visible, electrochemical, immunological, particle/energy measurement including any of alpha, beta or gamma energy particle energy measurement, cytometry, spectroscopy or other detection or measuring systems and various combinations and modifications of these processes.

In one set of the experiments related to the present invention, square wave voltammetry performed with a handheld electrochemical detector, was utilized to determine the quantity of particular analytes in various sample solutions. In this particular embodiment the hand held analyzer was equipped with a custom-made working electrode, a platinum wire as the auxiliary electrode, and an Ag/AgCl electrode as the reference electrode. Superparamagnetic nanoparticles at a concentration of 0.1 g/L were dispersed into 0.5 mL sample solutions containing 25 vol % urine at a pH of 8.5 and various predetermined levels of lead (Pb). Preconcentration of the superparamagnetic nanoparticles was then performed when the electrode tip was immersed into 0.5 mL of sample solution containing magnetic nanoparticles ($DMSA-Fe_3O_4$) and the solution was continuously stirred using a vortex mixer. After preconcentration, various measurements were then performed under the following conditions to determine the quantity of Pb present in the sample.

| Parameters | Conditions |
|---|---|
| Sample | 0.5 mL of Pb sample (25 vol. % urine), pH 8.5 |
| Nanoparticles | 0.1 g/L of $DMSA-Fe_3O_4$ |
| Preconcentration | 90 s in stirred sample at open circuit |
| Electrolysis | −0.85 V, 60 s in 8 mL of 0.5M $HNO_3$ or HCl |
| Detection | scan from −0.70 V to −0.35 V in same acid |
| SWV parameters | Amplitude: 25 mV, increment: 2 mV, freq: 25 Hz |

All measurements were made at room temperature in an atmospheric environment. In many of the prior art embodiments, the detection of metal ions in urine has been problematic due to complicating factors such as protein competition and electrode fouling. However in these experiments a linear response was obtained from 0 to 50 ppb of Pb in a sample containing 25 vol. % urine, which is equivalent to 0 to 200 ppb of Pb in whole urine. This concentration range is relevant to urinary biomonitoring of Pb for both normal and exposure levels. For example, after EDTA infusion, a Pb excretion rate over 50 μg in 24-hour urine suggests an increased body burden as a result of past exposure to Pb[23]. Further experiments yielded excellent reproducibility (% R.S.D of 5.3 for seven measurements of 30 ppb Pb), and Pb concentrations in urine samples comparable to those measured by ICP-MS. Thus, the nanoparticles of the present invention enable not only simple sample preparation and analyte collection, but it also enables for reliable results to be obtained even in complex biological matrices wherein metals may be bound to organic molecules and proteins.

To show the capability of the sensors in detecting multiple metal ions, simultaneous detection of Cd, Pb, Cu, Ag, and Hg in as-received (non-filtered) river water (Columbia River, Richland, Wash.) and seawater (Sequim Bay, Wash.) were performed at the $DMSA-Fe_3O_4$-magnetic electrodes using the operating conditions described above. The concentrations of background and spiked metal ions in the waters were detected with both the $DMSA-Fe_3O_4$ sensors and ICP-MS for comparison. The results indicated that the sensitivity and reliability of the nanoparticle-based sensors of the present invention were similar to the sensitivity of the ICP-MS device, which is a substantially more complex and expensive method and device.

In one embodiment the method and device of the present invention are embodied in a portable analyzer that employs electrochemical detection of target analytes that have been captured by the superparamagnetic nanoparticles of the present invention. Such a device allows real-time analysis of metal ions in spot urine specimens, thus providing a novel approach for the rapid assessment of exposure to materials such as lead (Pb). A simple device and procedure will not only facilitate routine monitoring of toxic metal exposures in high-risk populations (e.g., industrial workers, children, and people living in polluted areas) to ensure that these exposures are below a threshold for inducing permanent damage to various organ systems, but also reduce the time and lower the costs of metal ion analysis for clinical diagnosis.

While various preferred embodiments of the invention are shown and described, it is to be distinctly understood that this invention is not limited thereto but may be variously embodied to practice within the scope of the following claims. From the foregoing description, it will be apparent that various changes may be made without departing from the spirit and scope of the invention as defined by the following claims.

What is claimed is:

1. A system for determining quantities of at least one target analyte in a solution comprising:
    at least one superparamagnetic nanoparticle having an outer surface with at least one surface-bound ligand which adheres to the at least one target analyte;
    a collection device for collecting the superparamagnetic nanoparticles from the solution; and
    an electrochemical analyzer to analyze the collected at least one target analyte bound to the superparamagnetic nanoparticles,
    wherein the target analyte is a heavy metal ion.

2. The system of claim 1 wherein the collection device is an electrode having a magnetic quality.

3. The system of claim 2 wherein the electrode is an electromagnet.

4. The system of claim 2 wherein the electrode is a permanent magnet.

5. The system of claim 4 wherein the electrochemical analyzer is a voltammetric detector.

6. A method for determining quantities of at least one target analyte in solution, wherein said target analyte is a heavy metal ion, said method comprising:
    placing at least one superparamagnetic nanoparticle into the solution, the superparamagnetic nanoparticle having an outer surface with at least one surface bound ligand which adheres to the at least one target analyte;
    collecting the at least one superparamagnetic nanoparticle utilizing a collection device; and
    detecting the collected at least one target analyte bound to the superparamagnetic nanoparticle with an electrochemical analyzer to determine the quantities of the at least one target analyte within the solution.

7. The method of claim 1 further comprising the step of removing the at least one superparamagnetic particles from the collection device.

8. The method of claim 1 wherein the step of collecting the at least one superparamagnetic nanoparticles is performed utilizing an electrode having a magnetic quality.

9. The method of claim 8 wherein said electrode is an electromagnet.

10. The method of claim 8 wherein said electrode is a permanent magnet.

11. The method of claim 6 wherein the quantities of the at least one target analyte are determined utilizing voltammetry.

12. The method of claim 6 further comprising the step of removing the at least one super paramagnetic nanoparticle from collection device to form a sample prior to detection of at the at least one target analyte.

13. The method of claim 6 wherein the step of placing the at least one superparamagnetic nanoparticle into the solution includes dispersing the at least one superparamagnetic nanoparticles in a generally uniform distribution pattern within the solution to maximize the exposure of the at least one nanoparticle to the at least one target analyte.

* * * * *

UNITED STATES PATENT AND TRADEMARK OFFICE
CERTIFICATE OF CORRECTION

Page 1 of 1

PATENT NO. : 8,679,458 B2
APPLICATION NO. : 11/936405
DATED : March 25, 2014
INVENTOR(S) : Wassana Yantasee et al.

It is certified that error appears in the above-identified patent and that said Letters Patent is hereby corrected as shown below:

Title Page:

Item (75) Inventors: Replace "Maryin G. Warner" with "Marvin G. Warner"

Signed and Sealed this
Seventeenth Day of June, 2014

Michelle K. Lee
*Deputy Director of the United States Patent and Trademark Office*